(12) United States Patent
Fargahi et al.

(10) Patent No.: US 8,167,854 B2
(45) Date of Patent: May 1, 2012

(54) IMPLANTABLE DRUG RESERVOIR AND DEVICE HAVING AN IMPLANTABLE DRUG RESERVOIR

(75) Inventors: Amir Fargahi, Buelach (CH); Michael Tittelbach, Nuremberg (DE); Claus Harder, Uttenreuth (DE)

(73) Assignee: Biotronik VI Patent AG, Baar (CH)

( * ) Notice: Subject to any disclaimer, the term of this patent is extended or adjusted under 35 U.S.C. 154(b) by 16 days.

(21) Appl. No.: 12/477,840

(22) Filed: Jun. 3, 2009

(65) Prior Publication Data

US 2009/0312721 A1    Dec. 17, 2009

(30) Foreign Application Priority Data

Jun. 12, 2008   (DE) ................. 10 2008 002 396

(51) Int. Cl.
*A61M 31/00* (2006.01)
(52) U.S. Cl. .................................. 604/288.01
(58) Field of Classification Search ........... 604/288.04
See application file for complete search history.

(56) References Cited

U.S. PATENT DOCUMENTS

| | | | | |
|---|---|---|---|---|
| 4,886,501 A | * | 12/1989 | Johnston et al. | 604/175 |
| 7,534,241 B2 | * | 5/2009 | Coppeta et al. | 604/891.1 |
| 2006/0025821 A1 | * | 2/2006 | Gelfand et al. | 607/3 |
| 2006/0067972 A1 | * | 3/2006 | Kesten et al. | 424/426 |
| 2006/0190039 A1 | * | 8/2006 | Birk et al. | 606/219 |
| 2009/0104243 A1 | * | 4/2009 | Utkhede et al. | 424/423 |

FOREIGN PATENT DOCUMENTS

| | | |
|---|---|---|
| EP | 1 488 761 A1 | 12/2004 |
| EP | 1 980 290 A1 | 10/2008 |
| WO | WO 85/02123 | 5/1985 |
| WO | WO 00/54745 | 9/2000 |
| WO | WO 2004/002681 A2 | 4/2004 |
| WO | WO 2004/030753 A1 | 4/2004 |
| WO | WO 2005/014084 A1 | 2/2005 |
| WO | WO 2005/037055 A2 | 4/2005 |
| WO | WO 2006/022790 A1 | 3/2006 |
| WO | WO 2007/051563 A1 | 5/2007 |
| WO | WO 2007/069696 A1 | 6/2007 |
| WO | WO 2007/138590 A2 | 12/2007 |

OTHER PUBLICATIONS

German search report for priority application DE 10 2008 002 396.5.
European search report for priority application EP 09 16 0147.

* cited by examiner

*Primary Examiner* — Nicholas Lucchesi
*Assistant Examiner* — Jason Flick
(74) *Attorney, Agent, or Firm* — Biotech Beach Law Group PC

(57) ABSTRACT

The invention relates to an implantable drug reservoir (10) having a cavity (28) enclosed by a sheathing (12) and arranged between a proximal end (14) and a distal end (16) for storing one or more drugs (50), having an outlet opening (24) for the drug(s) (50). The drug(s) (50) can be delivered to a delivery region (70) through a puncture device (20) at one end (16). The invention also relates to a device (100) having a drug reservoir (10).

14 Claims, 4 Drawing Sheets

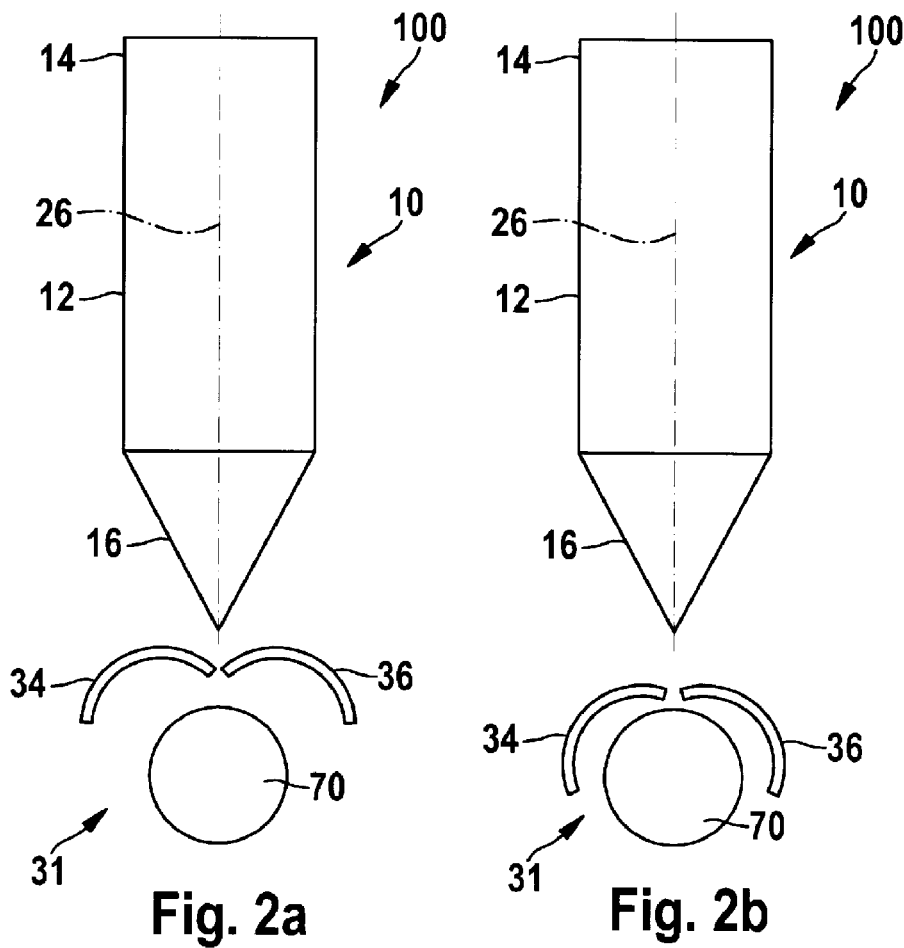
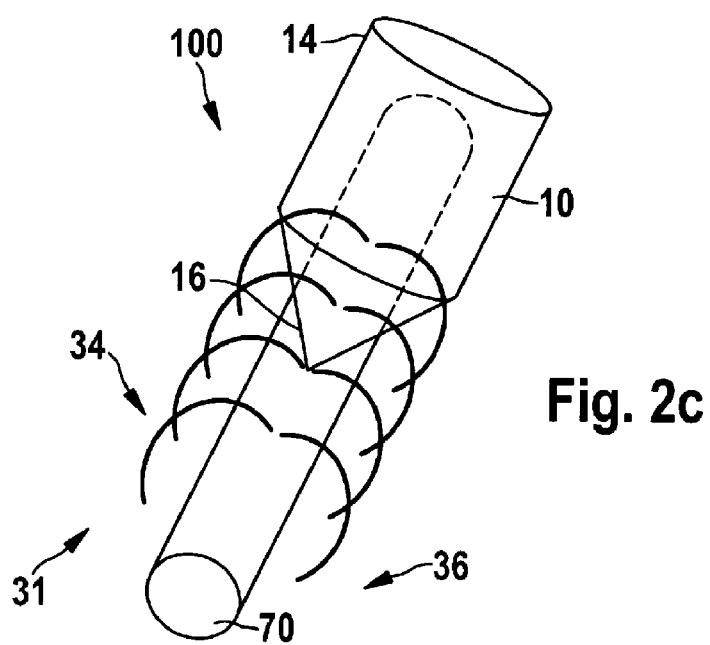

ns and devices having an implantable drug reservoir.

IMPLANTABLE DRUG RESERVOIR AND DEVICE HAVING AN IMPLANTABLE DRUG RESERVOIR

CROSS REFERENCE TO RELATED APPLICATIONS

This application claims benefit of priority to German patent application serial no DE 10 2008 002 396.5, filed Jun. 12, 2008; the entire contents of which are herein incorporated by reference in their entirety.

TECHNICAL FIELD

The invention relates to implantable drug reservoirs and devices having an implantable drug reservoir.

BACKGROUND OF THE INVENTION

Implantable devices for regional drug delivery through drug depots introduced transarterially are known. However, they are often unsuitable for delivering sufficiently large quantities of drug. Traditional drug pumps are large and require active control and therefore must be explanted after use. Therefore there remains a need to develop new devices for delivery of drugs.

SUMMARY OF THE INVENTION

The object of the invention is to create an implantable drug reservoir that can deliver large quantities of a drug to a delivery region, e.g., in an arterial vessel. This object is achieved according to the invention by the features of the independent claims. Advantageous embodiments and advantages of the invention are derived from the additional claims and description.

According to a first aspect of the present invention, an implantable drug reservoir is provided, having a cavity which is surrounded by a sheathing and arranged between a proximal end and a distal end for supplying the drug(s). At one end, a puncture device is provided, by means of which the drug(s) can be delivered into a drug delivery region. The drug(s) may be delivered automatically, e.g., into a blood vessel. A vascular wall can be punctured by the puncture device to deliver the drug within the vessel.

The puncture device may preferably be formed from a metallic material. The drug reservoir can be brought into contact with a vascular lumen, for example, by means of the puncture device and affixed there by the anchoring device. The anchoring device enables the drug reservoir to be wedged into the inner vascular lumen, e.g., by unfolding wings, spreading elements, hooks and the like. This allows secure placement of the drug reservoir and secure refilling of the drug reservoir, if necessary. The distal end of the drug reservoir may preferably have a conical course, a preferred conical angle being between 2° and 178°, preferably between 10° and 170°.

The drug reservoir may contain a sufficient quantity of drug, e.g., in the range of 2 mg to 100 mg. It may also be a single drug, a drug formulation or multiple drugs. These variants are referred to in generalized terms as drugs. Drugs may include, for example, immunosuppressants for treatment of transplanted organs, cytostatics for treatment of tumors, insulin and the like. The drug reservoir may remain in or on the delivery region and may be refilled, if necessary. The drug may advantageously be delivered into an arterial vessel, for example, by means of controllable elution kinetics or may diffuse or be forced out of the drug reservoir. Elution refers to a dissolution or release of one or more substances from a stationary, solid or liquid phase. A mobile phase consisting essentially of one or more solvents is passed by the stationary phase and a mixture (eluate) of solvents and dissolved substances is discharged.

The dimensions of the drug reservoir may be small, e.g., a diameter in the range of 1 mm and a length in the range of a few mm, e.g., 3 mm. These dimensions can easily be adapted to the delivery region and the intended use. Comparatively large quantities of drug may be administered. The drug may be administered into the arterial bloodstream to the diseased region directly proximally from a diseased area, so that the drug can be transported through the bloodstream to the diseased region. The drug reservoir may optionally be equipped with a defined conveyance mechanism or the drug substance may be delivered by diffusion. In both cases, the reservoir may be designed as a refillable depot. The drug reservoir may fundamentally be designed to be fully degradable, expediently with the exception of the anchoring device, so that explanation after use can be avoided.

An anchoring device with which the drug reservoir can be anchored in or on the drug delivery region is preferably provided. The drug reservoir with its puncture device can preferably be affixed there. This may be accomplished directly, whereby a suitable device having the drug reservoir is introduced there and is deployed in the delivery region and/or a counterelement may be released into the delivery region and the drug reservoir affixed there. The reservoir may advantageously be anchored inside a vessel through whose vascular wall the drug reservoir with its puncture device penetrates. The drug reservoir may be positioned reliably and in a targeted manner to remain in the drug delivery region over a long period of time.

According to an advantageous further embodiment, hooks are or may be formed on the distal end for anchoring the implant in or on the drug delivery region. To do so, wires which can be extended at the distal end for anchoring in or on the drug delivery region may preferably be arranged in the cavity. The wires may preferably be formed from a shape memory material, e.g., a nickel-titanium alloy, in particular nitinol, in at least some regions. The wires may advantageously be arranged within the drug reservoir on insertion of same so that they do not protrude at all on the distal end and protrude only slightly on the proximal end. The proximal end may expediently be provided with a cover through which the wires pass. If the drug reservoir has reached the desired delivery region, the wires can be advanced from the proximal end to the distal end, so that they protrude out of the outlet opening. Due to the properties of the shape memory material, the wires are then folded over at their free ends, thereby securely anchoring the drug reservoir in the delivery region.

The sheathing of the drug reservoir may advantageously be formed from a degradable polymer, so that explantation of the drug reservoir at a later point in time may be omitted.

According to an advantageous further embodiment, a swellable material may be arranged on the proximal end of the sheath, forcing the drug that is situated between the material and the distal end out of the outlet opening due to swelling. A porous closure can preferably close the sheathing on the proximal end. The swellable material may preferably be formed by a degradable polymer. Water can penetrate through the porous closure on the proximal end into the drug reservoir and cause the swellable material to swell up. This has the advantage that swelling of the swellable material can be controlled through the porosity, e.g., the number and/or size of pores. Therefore, the rate of release of the drug from the drug reservoir can in turn be influenced. A displaceable partition may advantageously be arranged between the swellable material and the drug, preventing mixing of the swellable material and the drug on the one hand while on the other hand controlling the release of the drug in a defined manner because any inhomogeneous swelling that might occur is homogenized by the partition in its effect on the drug.

A shoulder may advantageously be formed on the proximal end, widening in diameter in the direction away from the sheathing. The shoulder may preferably be designed to be radiopaque in at least some areas. The shoulder advantageously facilitates connection of a catheter or a cannula with which the drug reservoir can be filled or refilled. The shoulder, which widens in a funnel shape proximally, facilitates the insertion of the tip of a catheter into the drug reservoir. As the catheter approaches the drug reservoir, the shoulder guides the tip of the catheter to the proximal end of the drug reservoir, which may advantageously be sealed with a membrane, e.g., a TEFLON membrane. The tip of the catheter may be furnished with a syringe needle at its distal end, which can then puncture the membrane and fill the drug reservoir. On retraction of the syringe needle after filling, the membrane can seal the puncture site again. If the shoulder is designed to be radiopaque, this greatly simplifies the finding of the drug reservoir and the shoulder, which can then be tracked in real time, for example.

According to another aspect of the invention, a device having a drug reservoir with at least one of the features described above is proposed, in which at least one coupling element and/or stabilizing element is provided for coupling the drug reservoir in or on the drug delivery region. A reliable fixation of the drug reservoir can be achieved in this way. Then a coupling element, which can be locked onto the drug reservoir with its puncture device in particular, can be introduced, e.g., into a blood vessel. A distal end of the drug reservoir that tapers to a point can be secured on the coupling element in this way, e.g., by means of a simple snap mechanism on same. Such a coupling element may be advantageous, e.g., when a vascular wall that should be treated especially gently must be punctured. At the same time, the drug reservoir offers a greater volume for a drug because an anchoring device, which must be inserted into or with the drug reservoir, may be omitted.

Shell-shaped or rake-like wing elements may advantageously be provided as stabilizing elements or coupling elements across the longitudinal extent of the drug reservoir. The wing elements may be attached together to a hinge and moved toward one another with their free ends in order to enclose a portion of tissue, e.g., a section of a blood vessel, between them. The drug reservoir pushes at its distal end through the wing elements, e.g., in the area of a point of separation or a hinge. The wing elements can advantageously stabilize the tissue portion, e.g., a section of a blood vessel. The wing elements may be designed as tubes that have been cut open or in the manner of a rake. If the wing elements are closed and the enclosed delivery region has thus been stabilized, the drug reservoir with its puncture instrument may thus be brought into proximity and connected to any coupling elements in the delivery region or an anchoring device on the reservoir side may be deployed. For anchoring at least one coupling element in the delivery region, it is also possible to provide for anchoring of at least one coupling element in the delivery region, to which the distal end of the drug reservoir can be connected.

The invention is explained in greater detail below as an example on the basis of exemplary embodiments depicted in the drawings in schematic diagrams, in which

BRIEF DESCRIPTION OF THE DRAWINGS

FIGS. 2a-2d show preferred devices having a drug reservoir and coupling elements with wing elements like half-shells (FIGS. 2a, 2b) and like rakes (FIG. 2c), which as depicted in FIG. 2d may be hinged.

DETAILED DESCRIPTION OF PREFERRED EMBODIMENTS

Figure 1A:
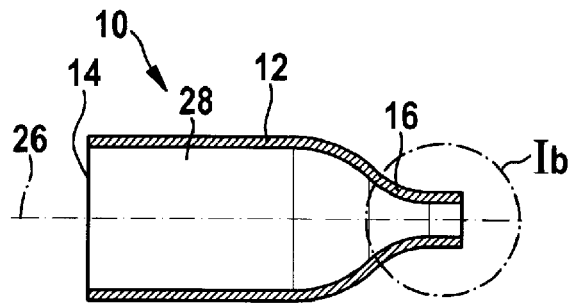
FIGS. 1a-1d show sectional diagrams of a preferred drug reservoir according to a first embodiment of the invention with an anchoring device made of a shape memory material having a detail (FIG. 1b) which is in different stages of insertion of the drug reservoir (FIGS. 1a, 1c, 1d).

Elements that are functionally the same or have the same effect are each labeled with the same reference numerals in the figures. The figures show schematic diagrams according to the invention. They illustrate nonspecific parameters of the invention. In addition, the figures show only typical embodiments of the invention and should not limit the invention to the embodiments shown here.

To explain the invention, FIGS. 1a-1d show a first exemplary embodiment of a preferred implantable drug reservoir 10 having a cavity 28 for storing one or more drugs 50 surrounded by a sheathing 12 and arranged between a proximal end 14 and a distal end 16. The drug reservoir 10 has an outlet opening 24 for the drug(s) 50. An anchoring device 30 with which the sheathing 12 and/or the drug reservoir 10 can be anchored in or on a drug delivery region (not shown) is provided. The drug reservoir 10 may be brought to an arterial vessel which forms the delivery region by passing it through extravascular tissue in particular. Drug can be released from the drug reservoir 10 into the bloodstream, transported away through it and to its site of action.

Figure 1B:
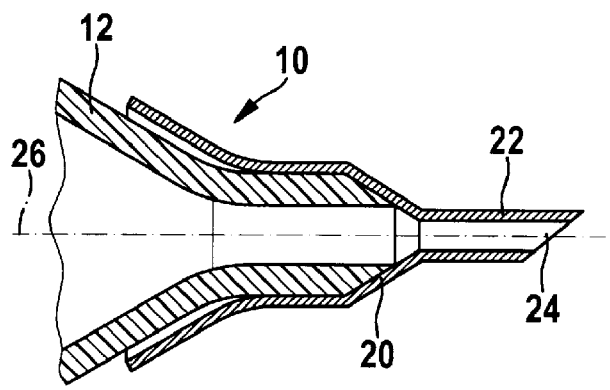

The drug reservoir 10 is designed in the form of a cylinder along its longitudinal extent 26 and tapers to a point on its distal end 16. The drug reservoir 10 has an outlet opening 24 on its distal end 16. The sheathing 12 may preferably be formed from a degradable polymer. On the distal end 16, a puncture device 20 having a syringe needle 22 with an outlet opening 24 is provided. The puncture device 20 may be integrated into or placed on the sheathing 12, as illustrated in FIG. 1b as a detailed view of FIG. 1a. The drug 50, which can escape out of the drug reservoir 10 through the syringe needle 22, is situated in the cavity 28. With the puncture device 20, the drug reservoir 10 penetrates through a vascular wall (not shown) and protrudes there into the inner lumen of the vessel into which the drug 50 is delivered and can be transported further in the bloodstream present there.

Figure 1C:
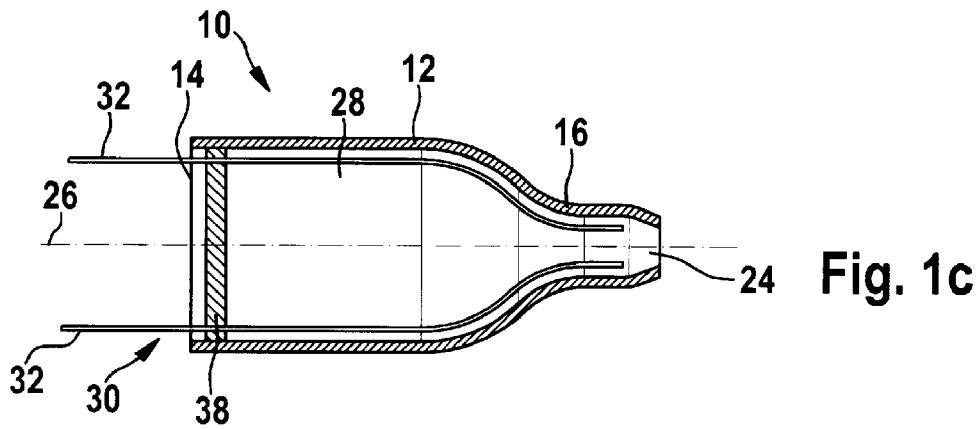

To allow anchoring of the drug reservoir 10 in the drug delivery region, wires 32 preferably made of a shape memory material, e.g., a nickel-titanium alloy (nitinol), are arranged in the cavity 28. The wires 32 may be arranged on the sheathing 12 on the inside circumference and may puncture through an otherwise preferably dense disk 38 as a cover on the proximal end 14. Before anchoring the drug reservoir 10, the wires 32 may protrude proximally beyond the proximal end 14, e.g., protruding by 1-5 mm, preferably 1.5 mm (FIG. 1c). The disk 38 seals the proximal end 14 with respect to the environment and is preferably arranged displaceably along the longitudinal extent 26 of the drug reservoir 10. The disk 38 may advantageously be formed from a degradable polymer. The sheathing 12 may expediently also be formed from a degradable polymer and the puncture device 20 may be made of a metallic material.

For anchoring in or on the drug delivery region, after the drug reservoir 10 has been positioned at the desired location and the puncture device 20 of the drug reservoir 10 has punctured through the vascular wall, for example, the wires 32 are advanced from the distal end 16 and/or the opening 24 by moving the disk 38 toward the distal end 16, whereby because of the properties of the shape memory material, they are folded outward and form hooks 33 protruding on the distal end 16 across the longitudinal axis 26, so that the drug reservoir 10 can be wedged and/or anchored in the vessel.

Favorable variants of preferred devices 100 having a drug reservoir 10 are shown in FIGS. 2a-2c. A preferred exemplary embodiment of the drug reservoir 10 has already been described in detail in conjunction with FIGS. 1a-1d, so that reference is made here to that description to avoid unnecessary repetition.

Figure 1D:
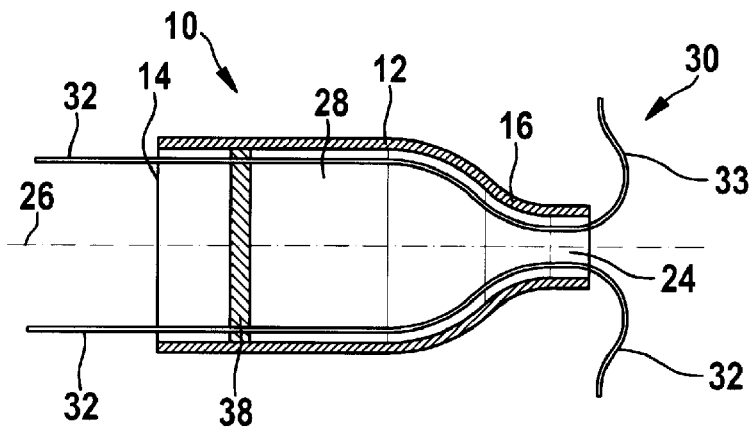
Figure 2D:
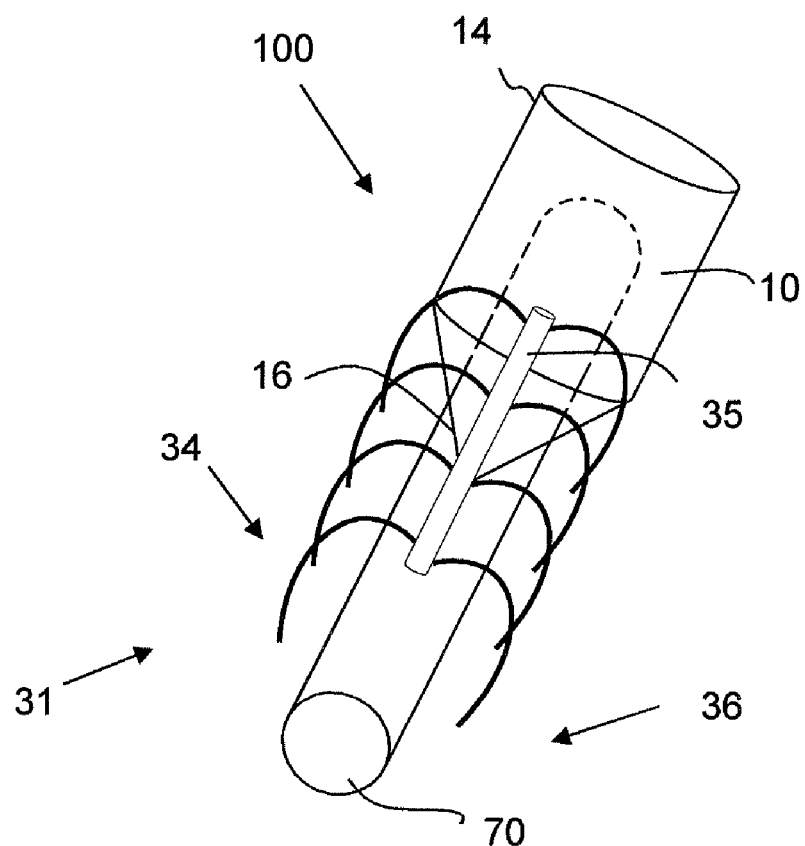

According to a preferred variant, for stabilizing the positioning of the drug reservoir 10, a stabilizing element 31 is provided, e.g., in the manner of half-shells 34, 36 of a tube that is cut open along its longitudinal extent and is aligned across the longitudinal axis 26 of the drug reservoir 10. The two half-shells 34, 36 are positioned on both sides of the target vascular section (delivery region 70) (FIG. 2a). The half-shells 34, 36 close around the target vascular section (FIG. 2b) by means of a mechanism that can be deployed from the outside and they do so by being pivoted about a hinge 35 (FIG. 2d) connecting the half-shells 34, 36 in the axial direction, for example. The vascular section stabilized in this way can then be punctured by the drug reservoir 10 and an anchoring device 30 may be deployed as illustrated in conjunction with FIGS. 1a-1d. Stable fixation of the drug reservoir 10 in the delivery region 70 is thus made possible.

The half-shells 34, 36 may be made of solid material or they may be designed in the form of a rake with individual segments shaped like arcs of a circle and spaced a distance apart in the axial direction, as indicated in FIG. 2c, or they may be formed from a woven or knit fabric, for example.

Additionally or alternatively, a coupling element may also be positioned inside the target vascular section (delivery region 70) upstream from application of the drug reservoir 10, so that the drug reservoir 10 can be locked in place by a simple snap mechanism. In this case, an anchoring device 30 may optionally be omitted (FIGS. 1c-1d).

The drug 50 can be released from the drug reservoir 10 in a variety of ways. The drug reservoir 10 releases the drug only by diffusion out of the cavity 28 through the syringe needle 22. The proximal end 14 of the drug reservoir 10 is closed. The drug reservoir 10 may have a membrane 42, preferably a TEFLON membrane, on its proximal end 14 by means of which the drug may be resupplied as needed by puncturing the membrane with a filling catheter. The drug reservoir 10 may be equipped with an automatic feed mechanism, so that the drug 50 can be delivered to the delivery region 70 without any external operation.

Figure 3:
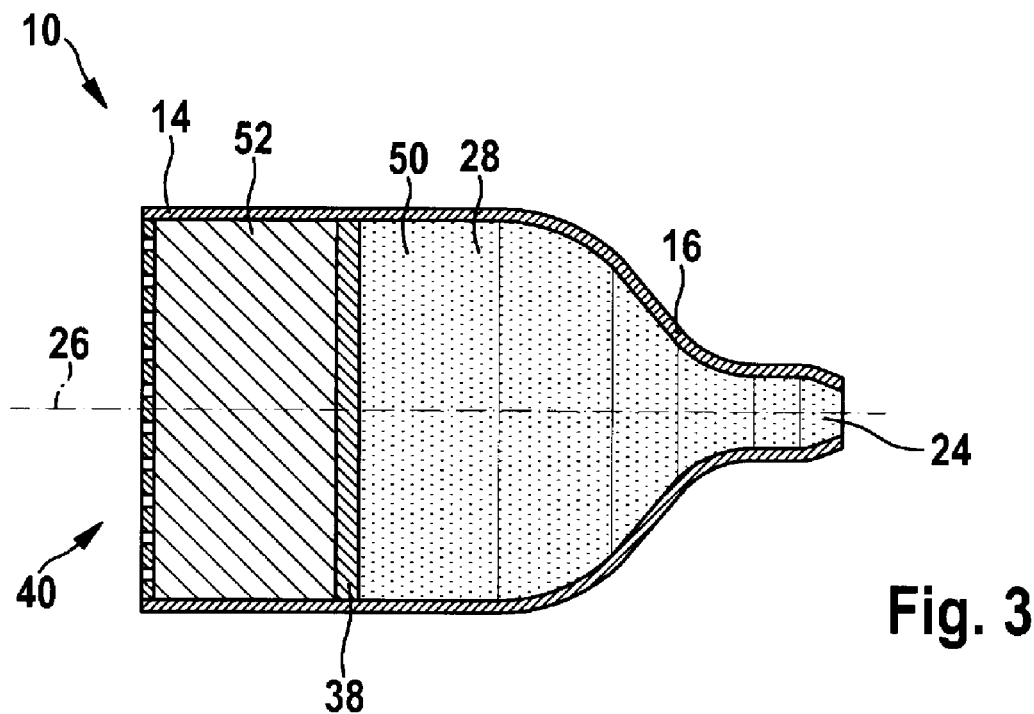
FIG. 3 shows a section through a preferred drug reservoir with a swellable material for expelling a drug out of the drug reservoir.

A preferred independent conveyor mechanism is diagrammed in FIG. 3. At the proximal end 14 of the sheathing 12 of the drug reservoir (FIGS. 1a-1d), a swellable material 52 is arranged in the cavity 28 of the drug reservoir 10, swelling under the influence of water and thereby taking up a larger volume than in the unswollen state. The swelling causes a drug situated between the material and the distal end 16 to be forced out of the outlet opening 24. A disk 38, which is punctured by wires 32 of an anchoring device 30 (not shown, see FIGS. 1c-1d), for example, is arranged between the swellable material 52 and the drug 50. If a pressure acts from the proximal end 14 on the disk 38, the latter forces a quantity of drug 50 out of the opening 24 in accordance with the pressure.

The swellable material 52 may be made of cellulose, for example. A porous closure 40 on the proximal end 14, which may be designed as a perforated disk, for example, closes the sheathing 12 and/or the drug reservoir 10. A desired input of liquid into the swellable material 52 can be adjusted through the porosity of the closure 40 and thus the swelling of the material can be regulated. The quantity of drug 50 coming out of the opening 24 can in turn be adjusted through the swelling of the swellable material 52. Due to the fact that the material can swell up with previously known kinetics, the release of the drug can be controlled with precision.

Figure 4:
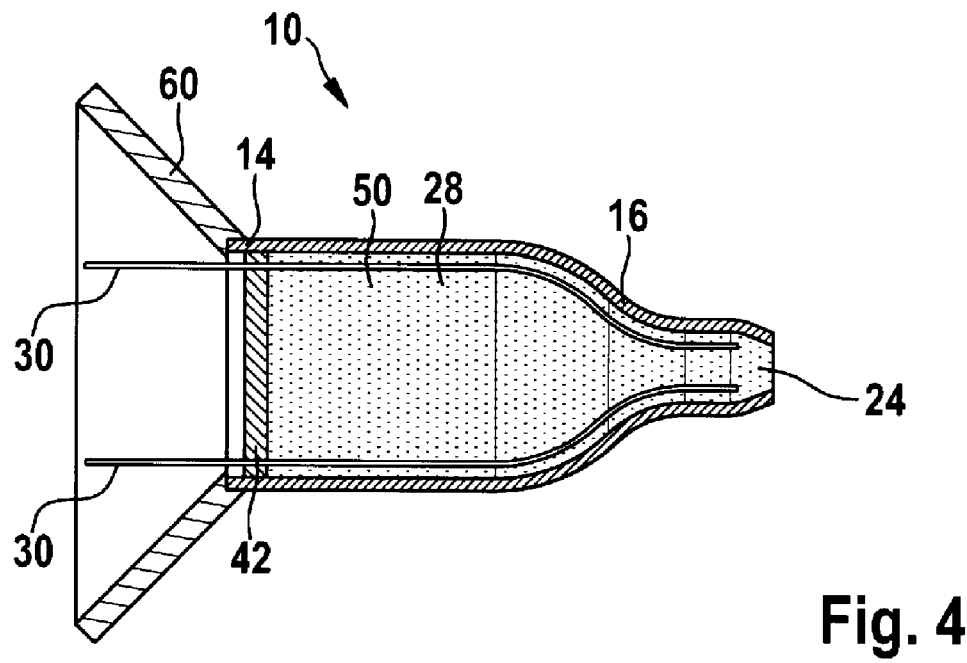
FIG. 4 shows a section through a preferred drug reservoir with an insertion aid for filling the drug reservoir.

FIG. 4 shows a preferred embodiment of a drug reservoir 10, in which subsequent filling of the drug reservoir 10 and/or refilling of the drug 50 is possible.

A shoulder 60 is formed on the proximal end 14, widening in diameter like a funnel from the proximal end 14. The shoulder 60 is radiopaque in at least some areas or is made entirely of a radiopaque material and can in this way be located easily from the outside. The proximal end 14 is closed with a membrane 42, preferably a TEFLON membrane. The shoulder 60 is connected to the membrane 42 in the proximal direction. The shoulder 60, which widens in a funnel shape, serves to position and guide a filling catheter (not shown) with a distal syringe needle with which the drug reservoir 10 in the inserted state can be filled with the drug 50 by puncturing the membrane 42 with the syringe needle. When the syringe needle is retracted, the membrane 42 closes again, so that the cavity 28 of the drug reservoir 10 is sealed from the outside again.

What is claimed is:

1. An implantable drug reservoir (10) having a cavity (28) surrounded by a sheathing (12) and arranged between a proximal end (14) and a distal end (16) for storing one or more drugs (50); and an outlet operating (24) for the drug(s) (50); characterized in that a puncture device (20) through which the drug(s) (50) can be delivered into a deliver region (70) is provided at one end 16 and the sheathing (12) is formed from a biodegradable polymer; characterized in that at least one coupling element and/or stabilizing element (31) is provided for coupling the drug reservoir (10) in or on the drug delivery region (70); and characterized in that wing elements (34, 36) are provided for stabilization across the longitudinal extent (26) of the drug reservoir (10), these wings being hinged along the longitudinal extent (26) and movable toward one another to enclose between them a portion of tissue to which the drug reservoir (10) can be connected at its distal end (16).

2. The device drug reservoir according to claim 1, characterized in that the wing elements (34, 36) are hinged together along the longitudinal extent (26).

3. The drug reservoir according to claim 1, characterized in that the puncture device (20) is formed from a metallic material.

4. The drug reservoir according to claim 1, characterized in that a swellable material is arranged in the cavity (28) on the proximal end (14), forcing the drug (50) which is between the swellable material and the distal end (16) out of the outlet opening (24) through swelling.

5. The drug reservoir according to claim 4, characterized in that a porous closure (40) on the proximal end (14) closes the cavity (28).

6. The drug reservoir according to claim 1, characterized in that a shoulder (60) which widens in diameter away from the sheathing (12) is formed on the proximal end (14).

7. The drug reservoir according to claim 6, characterized in that the shoulder (60) is designed to be radiopaque in at least some areas.

8. An implantable drug reservoir (10) having a cavity (28) surrounded by a sheathing (12) and arranged between a proximal end (14) and a distal end (16) for storing one or more drugs (50); and an outlet opening (24) for the drug(s) (50); characterized in that a puncture device (20) through which the drug(s) (50) can be delivered into a delivery region (70) is provided at one end (16) and the sheathing (12) is formed from a biodegradable polymer; characterized in that hooks (33) are or can be formed on the distal end (16) for anchoring on or in the drug delivery region (70); and characterized in that wires (32) which can be pushed through the outlet opening (24) on the distal end (16) for anchoring on or in the drug delivery region (70) extend through the cavity (28) to the proximal end (14) of the sheathing (12).

9. The drug reservoir according to claim 8, characterized in that the wires (32) are formed from shape memory material in at least some areas.

10. The drug reservoir according to claim 8, characterized in that the puncture device (20) is formed from a metallic material.

11. The drug reservoir according to claim 8, characterized in that a swellable material is arranged in the cavity (28) on the proximal end (14), forcing the drug (50) which is between the swellable material and the distal end (16) out of the outlet opening (24) through swelling.

12. The drug reservoir according to claim 11, characterized in that a porous closure (40) on the proximal end (14) closes the cavity (28).

13. The drug reservoir according to claim 8, characterized in that a shoulder (60) which widens in diameter away from the sheathing (12) is formed on the proximal end (14).

14. The drug reservoir according to claim 13, characterized in that the shoulder (60) is designed to be radiopaque in at least some areas.

* * * * *